United States Patent [19]
Bee et al.

[11] Patent Number: 5,990,932
[45] Date of Patent: Nov. 23, 1999

[54] COLLABORATIVE SHARED SPACE

[75] Inventors: James W. M. Bee, Ottawa; Doris D. Lamontagne, Napean; Gordon W. Hopkins, Kanata; Scott T. Smith, Kanata; Shaun Illingworth, Kanata, all of Canada

[73] Assignee: Northern Telecom, Limited, Canada

[21] Appl. No.: 08/995,539

[22] Filed: Dec. 22, 1997

[51] Int. Cl.[6] .................................................. H04N 7/14
[52] U.S. Cl. ........................... 348/15; 348/17; 379/93.21
[58] Field of Search .................................. 348/14, 15, 16, 348/17, 18, 36, 38, 39, 143, 159; 379/93.19, 93.21, 106.02; 370/260; 434/350, 307 R; 128/904, 920, 922, 903; 607/60

[56] References Cited

U.S. PATENT DOCUMENTS

| | | | |
|---|---|---|---|
| 4,516,156 | 5/1985 | Fabris et al. | 348/15 |
| 5,444,476 | 8/1995 | Conway | 348/15 |
| 5,448,285 | 9/1995 | Kadowaki | 379/93.19 |
| 5,508,713 | 4/1996 | Okouchi | 455/556 |

FOREIGN PATENT DOCUMENTS

| | | | |
|---|---|---|---|
| 406046479A | 2/1994 | Japan | H04Q 9/00 |

*Primary Examiner*—Curtis A. Kuntz
*Assistant Examiner*—Melur Ramakrishnaiah
*Attorney, Agent, or Firm*—Finnegan, Henderson, Farabow, Garrett & Dunner, L.L.P.

[57] ABSTRACT

In a video conference system, participants are provided with a greater sense of presence. A pair of monitors are positioned at each location and provide a presence view image and a shared space image of the other location. With this system, participants can overlap their finger pointing at a shared image while maintaining eye-to-eye contact.

25 Claims, 7 Drawing Sheets

COLLABORATIVE SHARED SPACE

BACKGROUND OF THE INVENTION

The present invention relates generally to video conferencing, and more particularly to a video conferencing system that provides a greater sense of presence between two or more people when communicating at a distance over a broadband network.

Video conferencing provides a system for users in remote locations to communicate both orally and visually. Typically, each location in a video conference includes a monitor and a camera. Each camera captures an image at its location and sends the image to the other location involved in the video conference. Each monitor receives the image from the camera of the other location and displays it to provide the users in each location with a video display of the other location. In addition, a voice communication link overlaps with the video images to transmit the voices of the participants simultaneously with the video image.

To provide a more intimate connection between participants in a video conference, some video conferencing systems have developed methods for providing participants with better eye-to-eye contact. Some of these systems use a camera placed behind a transparent/reflective panel. A video image projector projects the received image onto the mirrored or reflective side of the panel, which the participant then sees. At the same time, the camera captures the image of the participant at his eye-level through the non-mirrored or transparent side of the panel. The camera then sends this eye-level image of the participant to the video image projector of the similarly structured monitor at the other location. As a result, participants at both locations view each other at eye-level, thus providing eye-to-eye contact between the participants.

Although such video conferencing systems provide better eye-to-eye contact and an improved sense of presence between participants, these systems fail to provide participants with visual communication that is effective in all circumstances. For example, in a video conference between a medical specialist and a patient, current video conferencing systems do not take into account that the medical specialist needs to be aware of the patient's verbal and non-verbal feedback while looking at a general view and a close-up image of the patient at the same time. Further, current systems do not provide a mirror image of the participants to enable the specialist and the patient to focus on the same point of interest by overlapping their pointing and to verify the patient's complaint by pointing with a finger at different parts of the patient's body. In addition, these systems are not equipped to support a situation where the specialist needs to direct an assistant or cooperating physician by pointing at the patient's body.

Current video conference systems are ineffective in other circumstances as well, such as educational and training classes, which have requirements similar to the specialist/patient situation. For example, in a computer education class conducted by video conferencing, the instructor and student must be able to orient themselves with respect to points on either the instructor's or the student's computer screen.

SUMMARY OF THE INVENTION

Systems and methods consistent with the present invention provide a video conference system that gives participants a greater sense of presence. Further, the video conference enables participants to overlap their pointing at a shared image and facilitates eye-to-eye contact between the participants.

A video conference system, consistent with the present invention, includes a first monitor in the workspace for displaying a presence view image of the remote participant, a second monitor in the workspace for simultaneously displaying a shared space image showing a view in the remote location, and a controller for ensuring a continuous view of the presence view image and the shared space image in the workspace.

Both the foregoing general description and the following detailed description provide examples and explanations only. They do not restrict the claimed invention.

DESCRIPTION OF THE DRAWINGS

The accompanying drawings, which are incorporated in and constitute a part of this specification, illustrate embodiments consistent with the invention and, together with the description, explain the advantages and principles of the invention. In the drawings.

DESCRIPTION OF THE PREFERRED EMBODIMENT

Figure 1A:
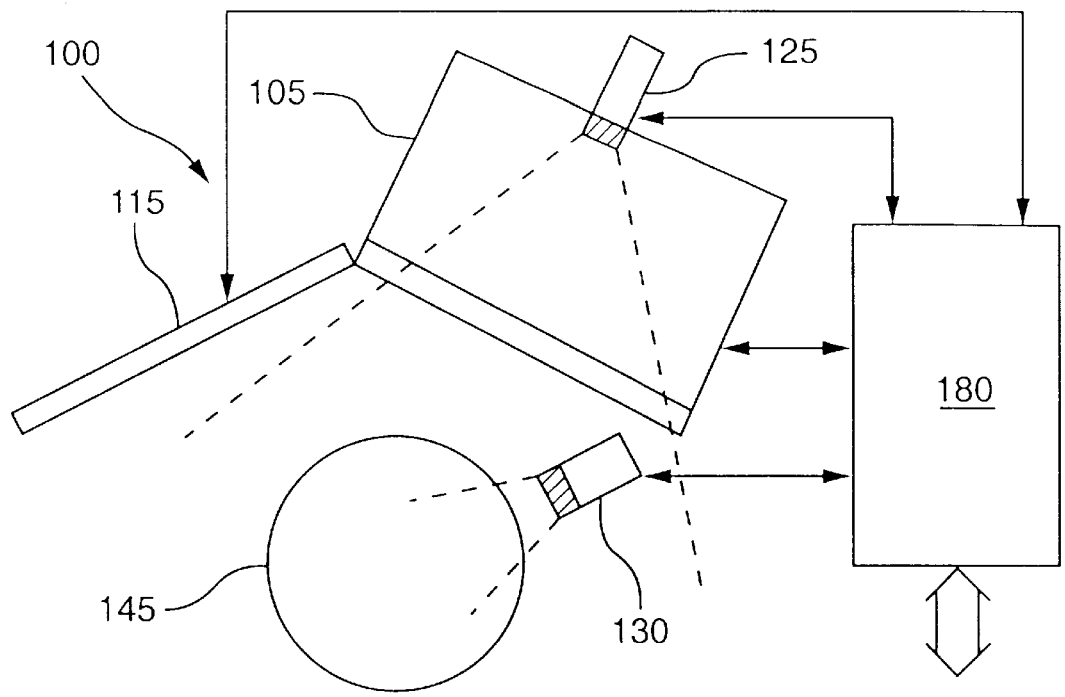
FIGS. 1A and 1B are diagrams of a plan view for a video conference system consistent with the present invention.

Reference will now be made to preferred embodiments of this invention, examples of which are shown in the accompanying drawings and will be obvious from the description of the invention. In the drawings, the same reference numbers represent the same or similar elements in the different drawings whenever possible.

Figure 1B:
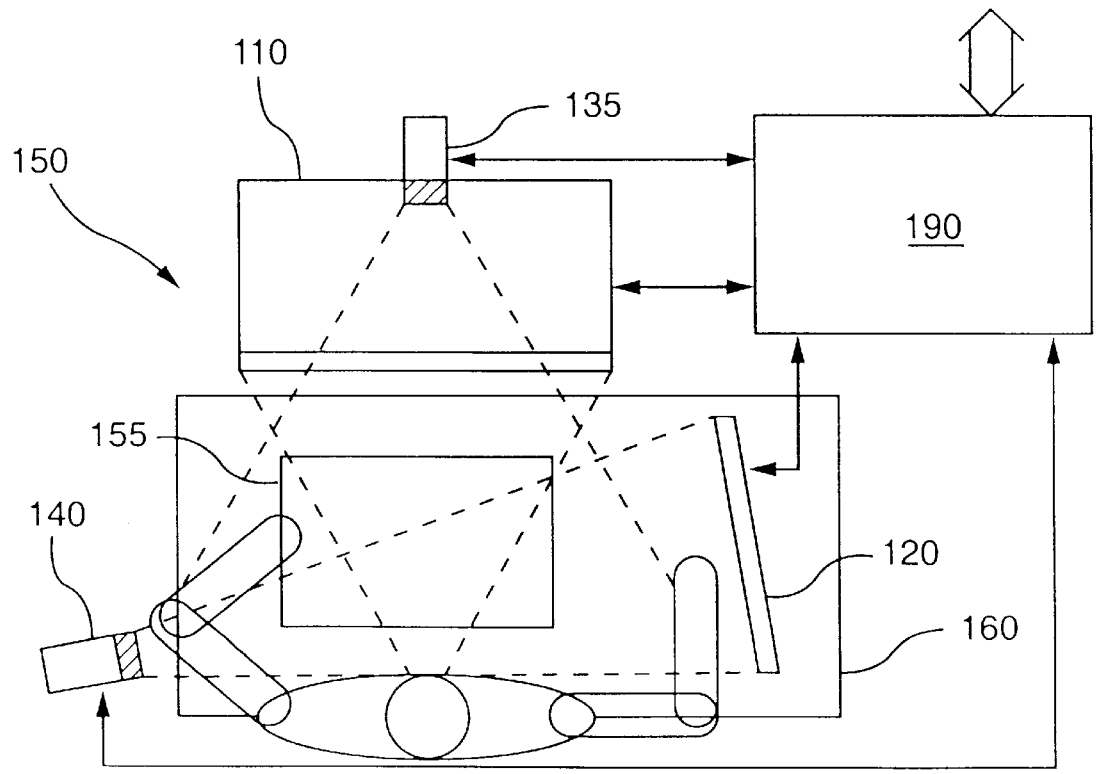
Figure 2A:
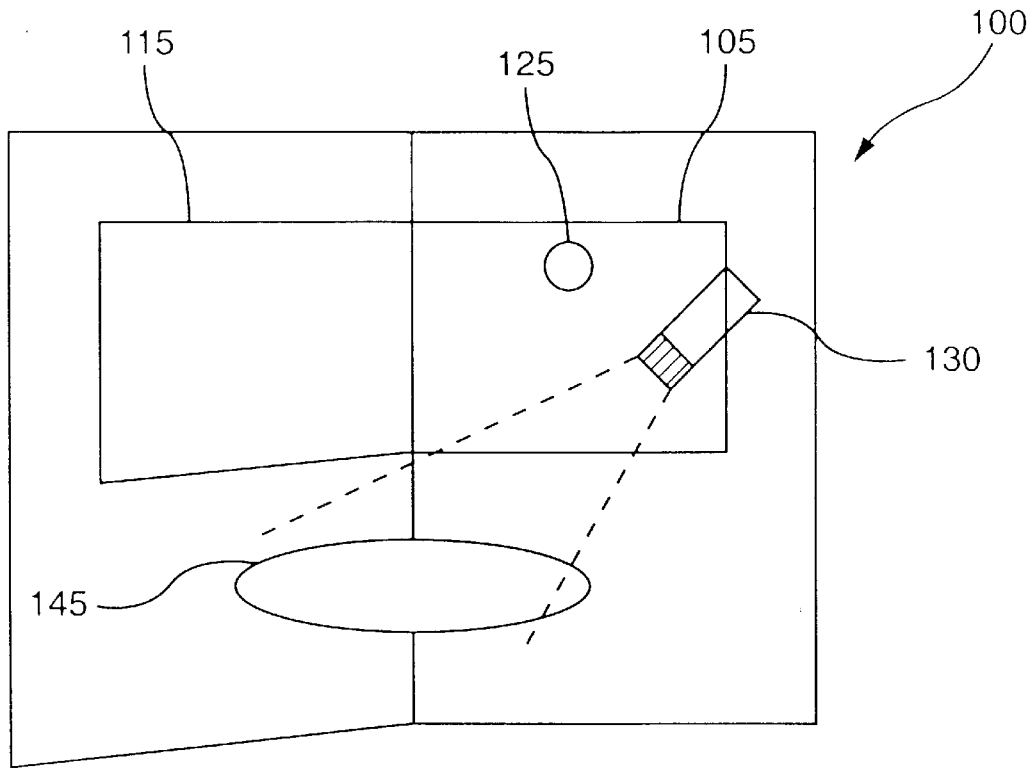
FIGS. 2A and 2B are diagrams of an elevation view of a the video conference system of FIGS. 1A and 1B.
Figure 2B:
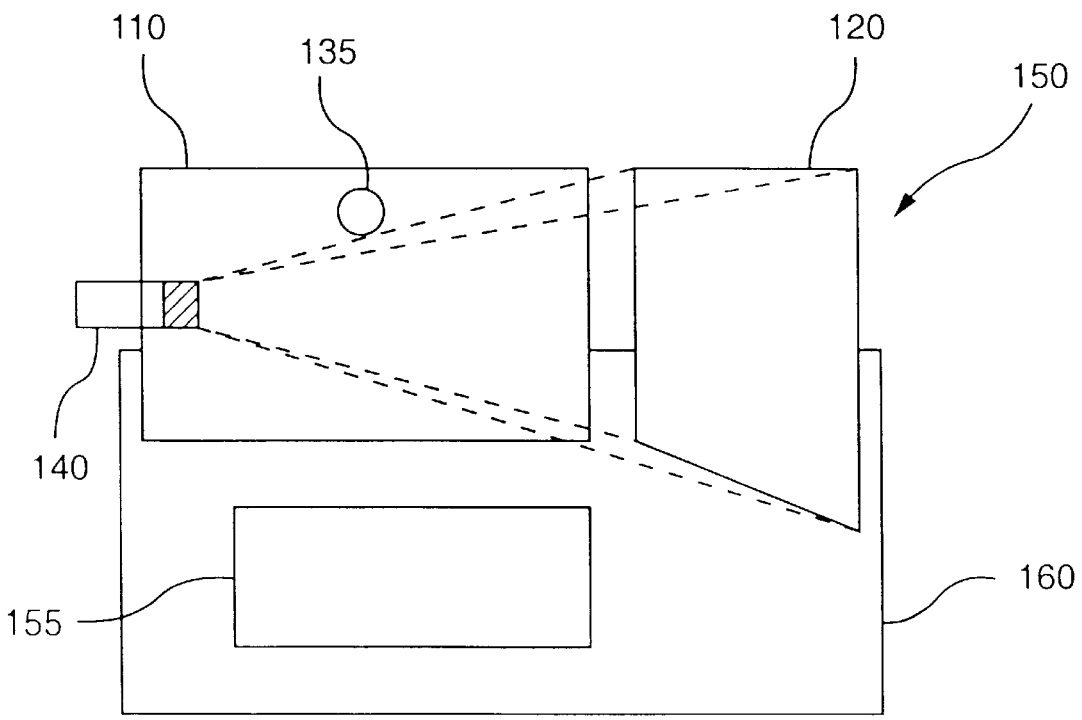

FIGS. 1A and 1B show diagrams of a plan view of a video conference system, consistent with the present invention. FIG. 1A shows a diagram of a patient examination room 100, and FIG. 1B shows a diagram of a specialist workstation 150. Examination room 100 includes two monitors 105 and 115, two cameras 125 and 130, an examination area 145, and a controller 180. Workstation 150 similarly includes two monitors 110 and 120, two cameras 135 and 140, and a controller 190. Workstation 150 also includes a computer interface 155 and a stand or desk 160. FIGS. 2A and 2B show an elevation view of the video conference system of FIGS. 1A and 1B. The elements shown in FIGS. 2A and 2B are identical to the elements shown in FIGS. 1A and 1B. For reasons of simplicity, controllers 180 and 190 are not shown in FIGS. 2A and 2B.

A camera at one location provides a picture displayed by a corresponding monitor at the other location. For example, cameras 125 and 130 in examination room 100 provide the images for monitors 110 and 120, respectively, at workstation 150. Similarly, cameras 135 and 140 at workstation 150 provide the images for monitors 105 and 115, respectively, in examination room 100. In addition to displaying the image provided by camera 130, monitor 120 is coupled to computer interface 155 by way of a data switch (not shown). All of the monitors at both locations are generally high resolution video monitors. Computer interface 155 preferably includes a PC or other computer as well as an interface device for using the computer.

To establish the channels of communication for transmitting video signals between the cameras and monitors, examination room 100 and workstation 150 each include a controller. As shown in FIG. 1A, controller 180 is coupled to monitors 105 and 115, cameras 125 and 130, and a computer (not shown). Similarly, as shown in FIG. 1B, controller 190 is coupled to monitors 110 and 120 and cameras 135 and 140. Although not shown, controller 190 is also connected to computer interface 155.

Controllers 180 and 190 are preferably computer-controlled switches that are directed by a computer at one of the locations of the video conference to establish the channels of communication between the locations. For example, the participant at workstation 150 may use computer interface 155 to instruct controller 190 to establish two bi-directional channels of communication for continuously and simultaneously transmitting the images from the cameras between the locations. After receiving the instruction, controller 190 contacts controller 180 to establish the channels. The channels are established if the controllers determine that there is sufficient available bandwidth. In addition to the channels for transmitting the video signals, controllers 180 and 190 also establish a general audio channel for transmitting sound signals between the locations.

Before sending a camera's video signal to the monitor, a video processor prepares the video signal for transmission to the corresponding monitor. A similar processor receives the transmitted signal and prepares it for display on the monitor. The processor may be, for example, a codex, which usually has some level of compression to improve transmission bandwidth.

After the bandwidth has been assigned, the video conference system has cameras 125 and 135 provide "presence" images of examination room 100 and workstation 150, respectively. For example, camera 135 is set to capture the image of the participant at workstation 150, such as the specialist, for display on monitor 105. Camera 125, on the other hand, is set to capture the image of the participant in examination room 100, such as the patient, for display on monitor 110. These "presence" images provide the participants with a sense of presence of each other. Controllers 180 and 190 ensure that the presence images are continuously received by each location.

Cameras 125 and 135 can be incorporated into monitors 105 and 110, respectively, in a manner consistent with conventional systems. Generally, cameras 125 and 135 are set in fixed positions when they are incorporated into the respective monitors. Monitors 105 and 110 are adjustable to enable the participants at the two locations to maintain eye-to-eye contact by setting the position of the monitors at the eye level of each participant. The vertical adjustment of the monitors can be provided, for example, by a simple hydraulic system to move the monitors up and down.

Camera 130 in examination room 100 preferably provides an image of a close-up view of a point of interest in examination room 100. Unlike camera 125, however, the position of camera 130 is not fixed. The gross positional setting of camera 130 can be preset in a particular location of examination room 100 or can be moved manually, such as by an assistant, to the particular point of interest. For example, if a specialist was interested in examining the knee of the patient, the specialist could direct the assistant to move the camera to a position adjacent the patient's knee. To provide this manual movement, camera 130 can be connected to a movable arm or some type of movable support that allows for camera 130 to be placed in positions adjacent to examination area 145 and the point of interest.

In addition to gross positional setting, camera 130 can have a fine positional setting as well, which can be adjusted, for example, by remote control in examination room 100 or by remote control in workstation 150. Such control can be by a separate device (not shown) or by computer interface 155. Like the fine positional setting, the zoom position of camera 130 can also be adjusted by a participant in examination 100 or remotely by a specialist at workstation 150 using, for example, computer interface 155.

Although camera 140 is set in a fixed position, it is preferably not incorporated into a monitor like cameras 125 and 135. The position and zoom of camera 140 is set to capture the image appearing on the screen of monitor 120, as well as anything appearing between camera 140 and monitor 120. As a result, if a participant at workstation 150 points to the screen of monitor 120, participants in examination room 100 will see the exact location of the pointing on monitor 115.

Monitors 115 and 120 can thus be referred to as "shared space" monitors, because they allow the participants in both locations to overlap their finger pointing on the same image. For example, the specialist at workstation 150 can point to the image of a certain part of the patient's body, which the assistant and patient can see on monitor 115, and ask the patient if he feels any pain there or to direct the assistant to examine or take a measurement of that part. The patient can indicate the exact location where the patient feels pain to the specialist by pointing with his finger, which the specialist views on monitor 120 and which the patient views on monitor 115 so that each sees the other's finger pointing at the same close-up view from camera 130. Controllers 180 and 190 also ensure that the shared space images on monitors 115 and 120 are continuously displayed at each location simultaneously with the presence images on monitors 105 and 110.

Figure 3:
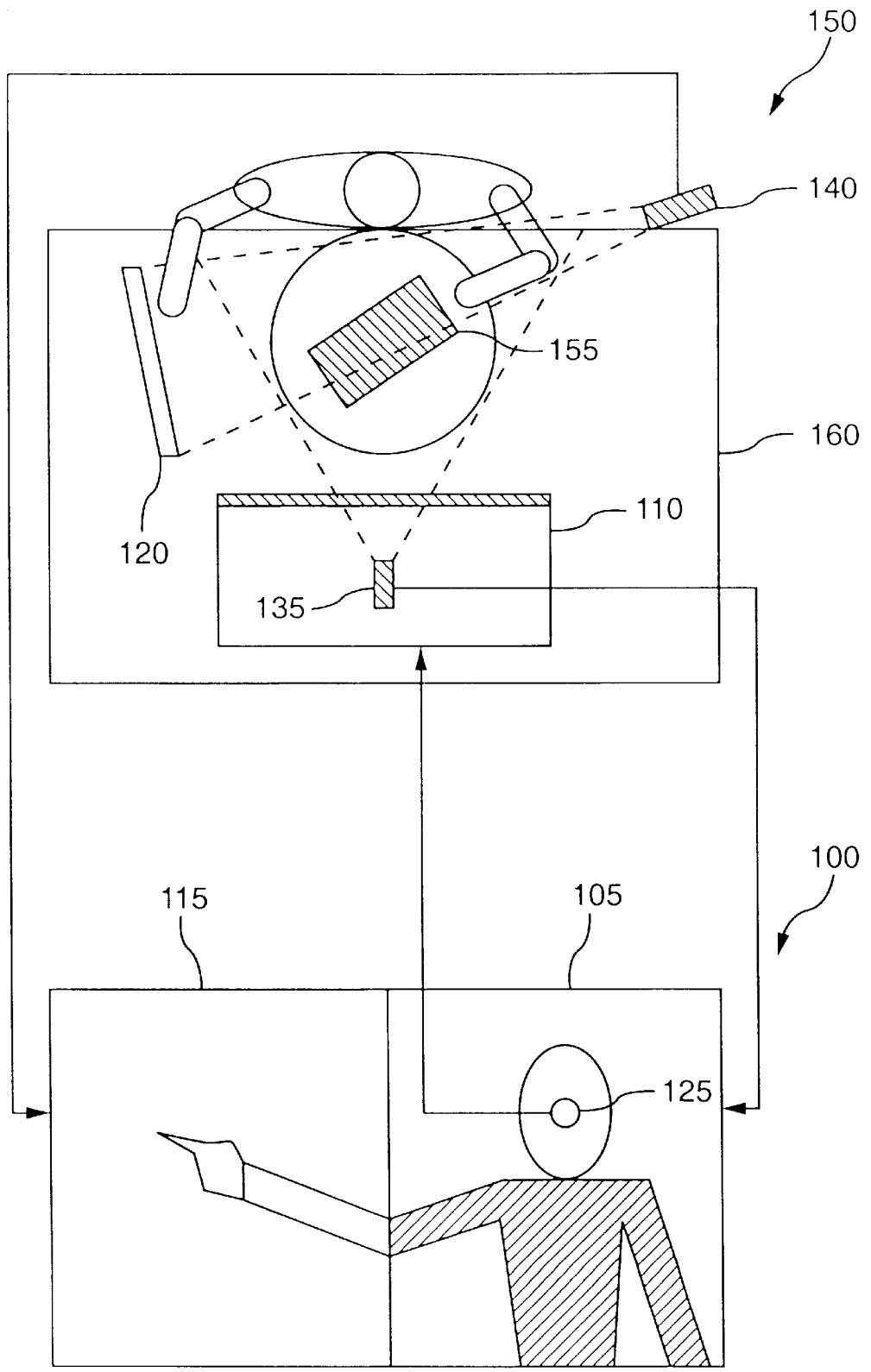
FIG. 3 is a diagram combining a plan view of a specialist's workstation with a front view of an examination room's monitors.

To provide an even greater sense of presence to the participants in examination room 100, cameras 135 and 140 can be positioned to show a continuous image of the participant at workstation 150 on monitors 105 and 115. FIG. 3 shows a diagram combining a plan view of workstation 150 with a front view of monitors 105 and 115 in examination room 100. To provide the continuous image of the participant at workstation 150 on monitors 105 and 115 as shown in FIG. 3, the positioning of cameras 135 and 140 must be set according to predetermined geometric relationships. Camera 135, which provides a presence view image to monitor 105, is positioned to show the upper torso of the participant at workstation 150 on monitor 105. Camera 140, which provides the shared space image to monitor 115, must be positioned to capture the image of the participant's right arm in front of monitor 120 (or left arm if camera 140 and monitor 120 are switched to opposite sides) that is not captured by camera 135. In addition, the zoom and distance of camera 140 from monitor 120 must also be appropriately set so that the proportion of the arm shown on monitor 115 coincides with the proportion of the arm shown on monitor 105. With such positional settings of cameras 135 and 140, the participants in examination room 100 can maintain eye contact and orient their pointing while looking at a continuous image of the participant at workstation 150.

In addition to showing close-up images of a point of interest in examination room 100, monitor 120 can also display text and image data held in a database. Generally, monitor 120 displays the video image captured by camera 130. As discussed above, this shared space image enables the participants at both locations to orient their pointing with respect to a point of interest in examination room 100.

Figure 4:
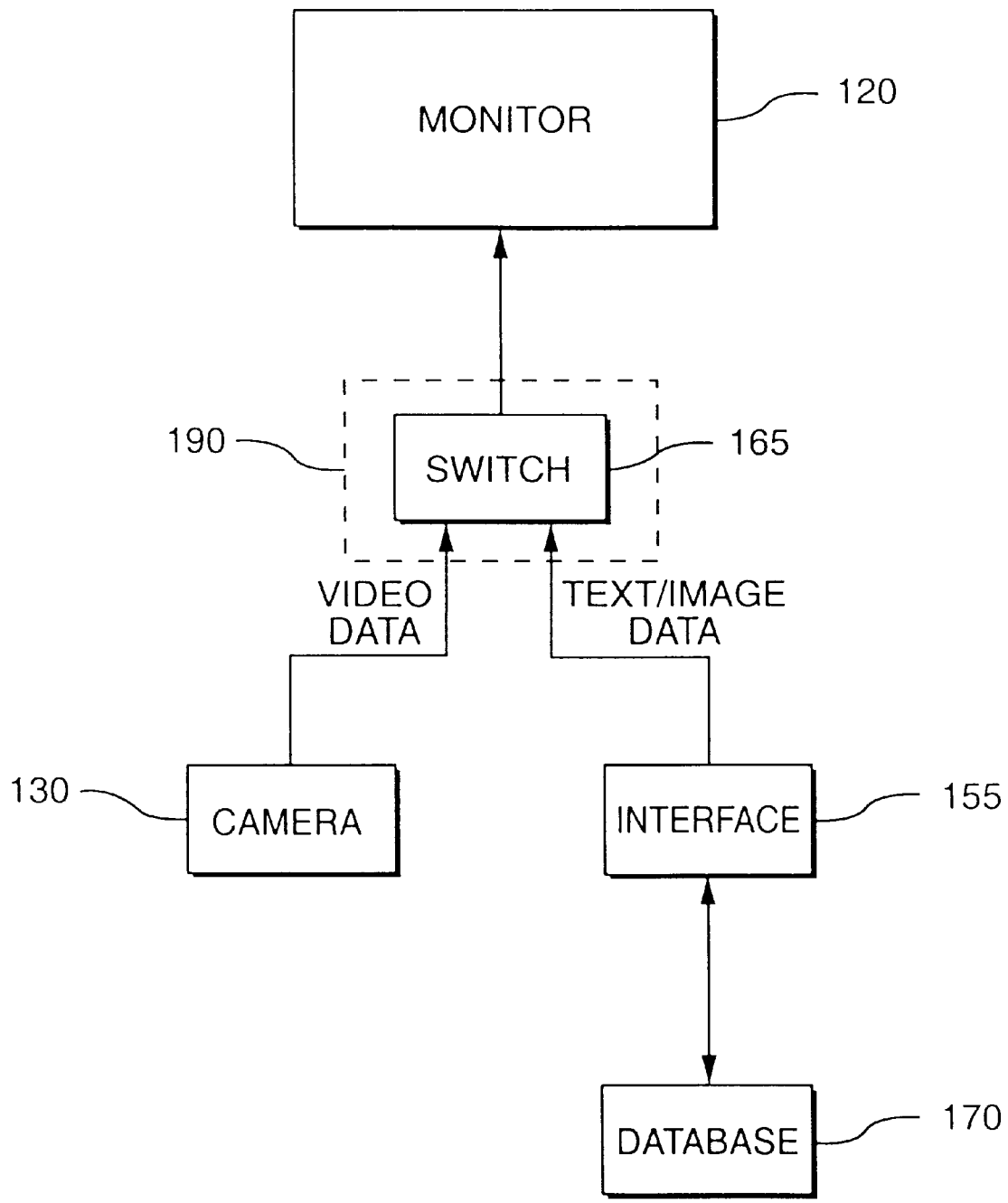
FIG. 4 is a block diagram of a switching system for displaying either video images or text/image data on a monitor consistent with the present invention.

In certain contexts, however, there may be information accessible only by the participant at workstation 150, which is of interest to the participants at all locations. FIG. 4 shows a block diagram of a switching system for displaying either video images or text/image data on a monitor consistent with the present invention. As shown in FIG. 4, a data switch 165, such as an application controller, is coupled to receive the video image from camera 130 and may be included within controller 190. Data switch 165 also receives text or image data from computer interface 155, which provides this data by accessing a memory having a database 170. Monitor 120 is coupled to data switch 165 and displays the video data or the text/image data according to the setting of data switch 165.

Figure 5:
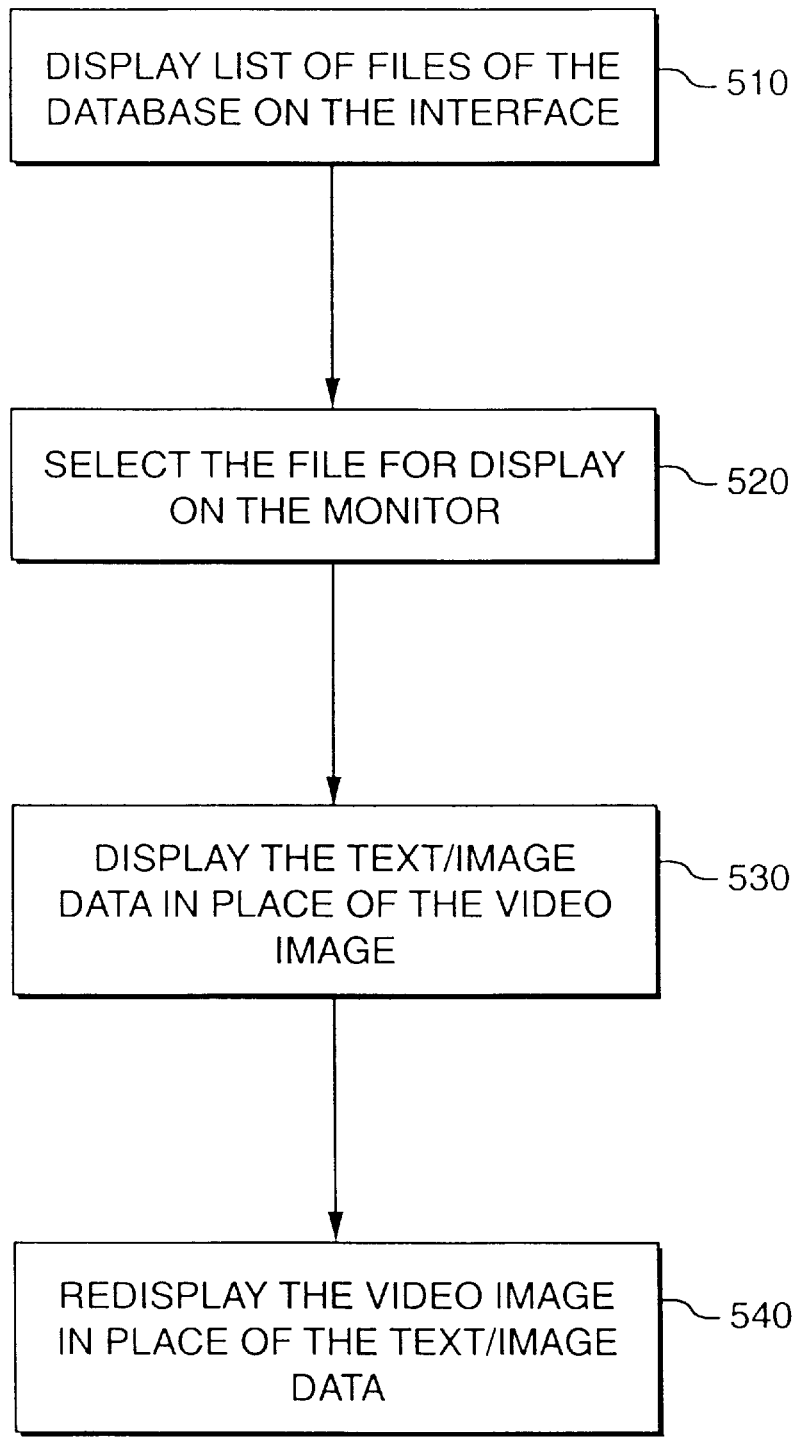
FIG. 5 is a flowchart showing a method, consistent with the present invention, for switching the display of a monitor to show either video data or text/image data.

Generally, data switch 165 is set by default to display the video image from camera 130. To change the display of monitor 120 to show text or image data, a participant uses computer interface 155 to access database 170. FIG. 5 shows steps, consistent with the present invention, for changing the setting of data switch 165 to show either the video data or the text/image data. First, the participant calls up the directory or list of files of database 170 onto computer interface 155 (step 510). Computer interface 155 may include, for example, a screen having a touch surface, which allows the specialist to call up and change directories by touching the screen. However, pointing devices such as a pen or a mouse, as well as more conventional devices such as a keyboard, may also be used to access database 170 through computer interface 155. The participant then selects the file or record for display by touching the appropriate location on the touch surface (step 520). The selection of the file causes the file to be displayed on computer interface 155. After selecting a particular file, the specialist touches the file on the screen of computer interface 155 and slides it in the direction of monitor 120 (step 530). This action sends a signal to data switch 165 to change its setting so that the file selected by the specialist is displayed on monitor 120, thus causing the selected file to "pop up" on monitor 120.

Like computer interface 155, monitor 120 also preferably includes a touch-sensitive screen. To redisplay the video image from camera 130, the specialist touches the screen of monitor 120 and slides the file down the screen (step 540). The touch and slide down the screen causes the file to reappear on computer interface 155.

When the specialist selects a file for display on monitor 120, the specialist can display both the video image and the file image in separate windows at the same time on monitor 120, either side by side or one on top of the other. Where the file image window is on top of the video image window, the specialist can touch the window of the video image and have the video image appear on top of the file image, and vise versa. Either or both windows may be translucent, so that when they overlap, the images align with each other. For example, a video image of a patient's leg could line up with an X-ray of the patient's leg. In this way, the specialist can move back and forth between the images.

In the context of a specialist and a patient, computer interface 155 enables the specialist to call up patient record files on the screen of computer interface 155, such as patient charts, X-rays, and other patient-related information. Using the above mentioned procedure, the specialist can display a chart on the shared space monitor. The specialist can use his finger to point out essential information and explain the meaning of the charts and images to the patient. In addition, the specialist can also update the records based on information obtained during the examination. To update the records, the specialist can use a pen-type pointing device to make notations by "writing" on computer interface 155 or by typing with a keyboard. The notations made by the specialist update the file held in database 170 when the record is returned to database 170.

The specialist at workstation 150 is also provided with a remote control device, which enables the specialist to adjust the fine positional movement of camera 130 in any direction. The device allows the specialist to control the zoom of camera 130 in a manner similar to the movement. These functions of the remote control device can be provide, for example, in a window of computer interface 155.

In the context of a video conference between a specialist and a patient, it may be necessary to gather information regarding the present condition of the patient. To provide this information, examination room 100 preferably includes a variety of diagnostic equipment with which an assistant in examination room 100 can examine the patient. The information obtained from the examination is shared simultaneously with the specialist at the remote location. For example, a stethoscope plugged into monitor 115 transmits the sound signal it obtains to the specialist at workstation 150. The specialist can listen to the sound signal from the stethoscope with a headset, through a speaker or through a stethoscope in workstation 150. While listening to the sound signal, the specialist can mute the sound of the rest of examination room 100. Using computer interface 155, the specialist may "record" this information and add it to the patient record.

Preferably, the video conference system consistent with the present invention has a channel for providing a general audio signal between examination room 100 and workstation 150. To provide the communication signal obtained from the diagnostic equipment to the specialist, controllers 180 and 190 can establish an additional channel dedicated to transmitting the signal of the diagnostic equipment, such as an audio signal from a stethoscope. Video signals and audio/visual signals, such as from a videotape, will generally use the shared space audio/visual channel.

Figure 6A:
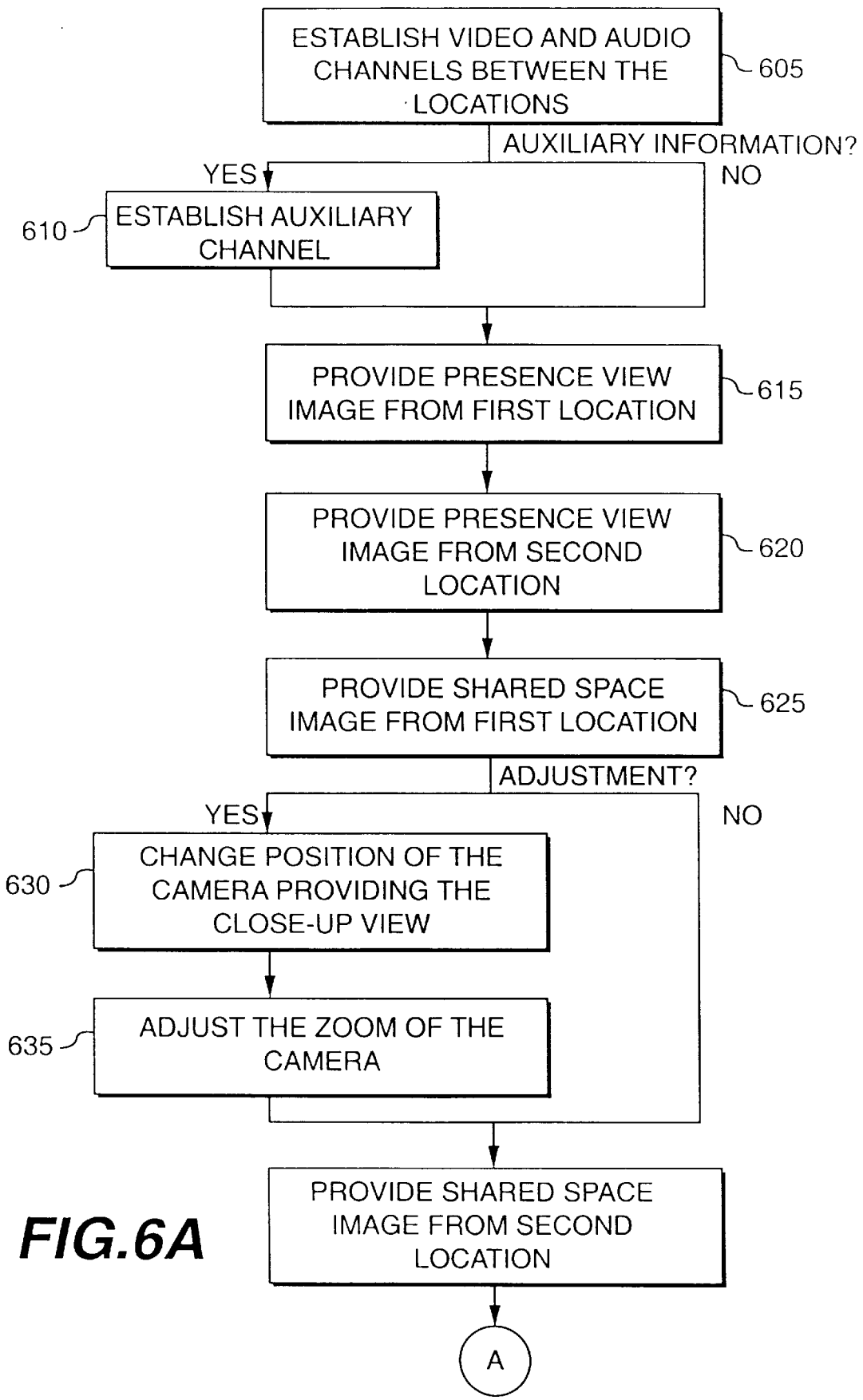
FIGS. 6A and 6B are flowcharts showing a method for providing a video conference consistent with the present invention.
Figure 6B:
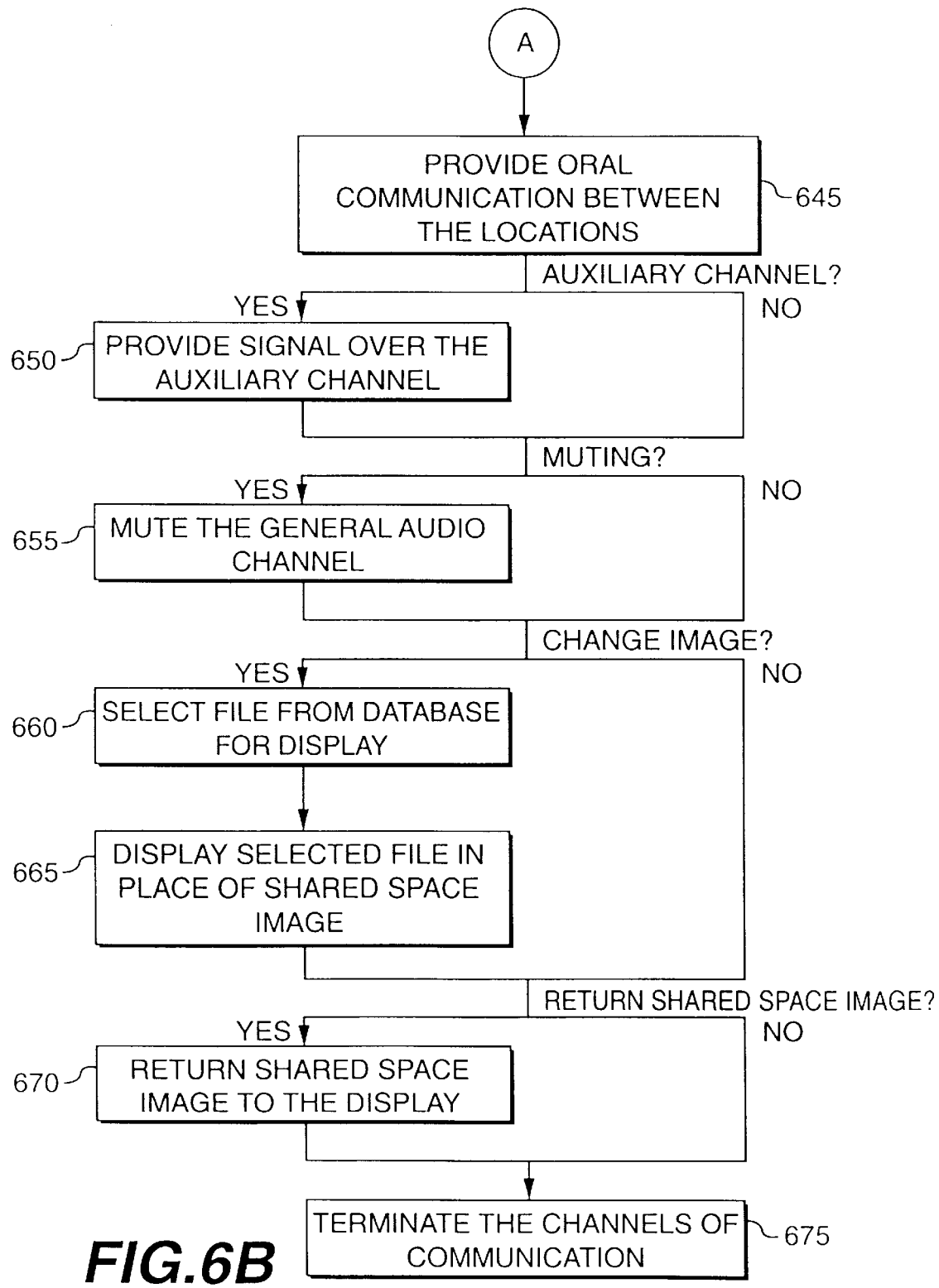

FIGS. 6A and 6B contain a flow chart showing steps for implementing a video conference system, consistent with the present invention. To begin the video conference, the channels of communication must first be established. Controllers 180 and 190, as instructed by a computer at either location of the video conference, establish several channels between the locations of the video conference including a bi-directional video channel for providing images to the presence view monitors, a bi-directional video channel for providing images to the shared space monitors, and a bi-directional general audio channel between the two locations (step 605). In addition, a dedicated audio channel for transmitting auxiliary information, such as diagnostic information between examination room 100 and workstation 150, may also be established (step 610).

The video channel between the presence view monitors provides an image of examination room 100 for display on monitor 110 (step 615). This video channel also sends an image of workstation 150 for display on monitor 105 (step 620). At the same time, the video channel between the shared space monitors provides a close-up view of a point of interest in examination room 100 to monitor 120 (step 625). To adjust the close-up view, a participant in examination room 100 or at workstation 150 may adjust the position of a camera providing the close-up view (step 630). In addition, either participant can adjust the zoom of the camera (step 635). Camera 140 uses the shared space video channel to transmit an image of monitor 120 for display on monitor 115 (step 640).

Using the general audio channel, the oral communication is transmitted back and forth between examination room 100 and workstation 150 (step 645). In addition, a signal from the diagnostic equipment is transmitted over the auxiliary audio channel if it has been established (step 650). If the participant at workstation 150 is receiving a signal over the auxiliary audio channel, the specialist can selectively mute the audio signal transmitted over the general audio channel (step 655). Otherwise, the signals transmitted over the general audio channel and over the auxiliary channel are presented at workstation 150 simultaneously.

In addition to selectively muting the audio signal received over the general audio channel, the specialist at workstation 150 may also change the image appearing on the shared space monitor 120. In particular, the participant selects an image or text file from a database, preferably using computer interface 155 (step 660). In response to an action by the specialist, the selected file is either displayed over or replaces the image of the close-up view coming from examination room 100 and shown on monitor 120 (step 665). Generally, the specialist changes the image from the close-up view to the selected file by touching the selected file on the screen of computer interface 155. The participant can then return the close-up view image to the screen of monitor 120, for example, by touching the selected file on monitor 120 and sliding it down the screen (step 670). Using controls in workstation 150, a specialist can take a picture or make a video recording of the close-up view appearing on monitor 120. The picture or video can be added to the patient record.

Finally, participants at either location can terminate the video conference by disconnecting the channels of communication (step 675). For example, the participant at workstation 150 may use computer interface 155 to instruct controller 190 to terminate the channels of communication.

CONCLUSION

A video conference system, consistent with the present invention, provides participants with a greater sense of presence. Further, the system enables participants to overlap their pointing at a shared image and facilitates eye-to-eye contact between the participants.

It will be apparent to those skilled in the art that various modifications and variations can be made without departing from the scope or spirit of the invention. Other embodiments of the invention will be apparent to those skilled in the art from consideration of the specification and practice of the embodiments of the invention disclosed herein. The specification and examples should be considered exemplary, with the true scope and spirit of the invention being indicated by the following claims and their full range of equivalents.

What is claimed is:

1. A video conferencing system in a workspace for communicating with a remote participant at a monitor in a remote location, the system comprising:
   a first monitor in the workspace for displaying a presence view image of the remote participant;
   a second monitor in the workspace for simultaneously displaying a shared space image showing a view in the remote location;
   a controller for ensuring a continuous view of the presence view image and the shared space image in the workspace; and
   transmitting means including a first camera positioned in the workspace and focused on the second monitor for transmitting the image of the second monitor to the remote location.

2. The video conferencing system according to claim 1, further comprising:
   a memory containing a database; and
   an interface, coupled to the controller, for providing access to the database.

3. The video conferencing system according to claim 2, wherein the controller includes
   a switch, coupled to the interface, for providing access to the database on one of the first and second monitors.

4. The video conferencing system according to claim 2, wherein the interface includes
   a touch surface for providing access to the database and selecting information from the database for display on the second monitor.

5. The video conferencing system according to claim 4, wherein the touch surface includes
   means for modifying the information of the database in response to a pointing device.

6. The video conferencing system according to claim 5, wherein the pointing device includes
   a pen-type pointing device.

7. The video conferencing system according to claim 1, further comprising:
   a second camera positioned in the workspace for transmitting a presence view image of a participant in the workspace to the remote location;
   a third camera positioned in the remote location for transmitting the presence view image of the remote participant to the first monitor; and
   a fourth camera positioned in the remote location for transmitting the shared space image showing the view in the remote location to the second monitor.

8. The video conferencing system according to claim 7, wherein the fourth camera includes
   means for adjusting the position of the fourth camera; and
   means for modifying the zoom of the fourth camera.

9. The video conferencing system according to claim 8, wherein the means for modifying the zoom of the fourth camera includes
   means for changing the zoom of the fourth camera remotely at the workspace.

10. A video conferencing system for a workspace and a remote location, the system comprising:
   a first monitor in the workspace for displaying a first presence view image of a remote participant in the remote location;
   a second monitor in the workspace for displaying a first shared space image showing a view in the remote location;
   a first controller for ensuring a continuous and simultaneous view of the first presence view image and the shared space image in the workspace;
   a third monitor in the remote location for displaying a second presence view image of a participant in the workspace;

a fourth monitor in the remote location for displaying a second shared space image showing a view of the second monitor;

a second controller for ensuring a continuous and simultaneous view of the second presence view image and the second shared space image in the remote location; and transmitting means including a first camera positioned in the workspace and focused on the second monitor for transmitting the image of the second monitor to the remote location.

11. The video conferencing system according to claim 10, further comprising:

a memory containing a database; and an interface, coupled to the first controller, for providing access to the database.

12. The video conferencing system according to claim 11, wherein the first controller includes a switch, coupled to the interface, for providing access to the database on one of the first and second monitors.

13. The video conferencing system according to claim 11, wherein the interface includes a touch surface for providing access to the database and selecting information from the database for display on the second monitor.

14. The video conferencing system according to claim 13, wherein the touch surface includes means for modifying the information of the database in response to a pointing device.

15. The video conferencing system according to claim 14, wherein the pointing device includes a pen-type pointing device.

16. The video conferencing system according to claim 10, further comprising:

a second camera positioned in the workspace and focused on a participant in the workspace;

a third camera positioned in the remote location for providing the presence view image of the remote participant to the first monitor; and a fourth camera positioned in the remote location for providing the shared space image showing the view in the remote location to the second monitor.

17. The video conferencing system according to claim 16, wherein the fourth camera includes means for adjusting the position of the fourth camera; and means for modifying the zoom of the fourth camera.

18. The video conferencing system according to claim 17, wherein the means for modifying the zoom of the fourth camera includes means for changing the zoom of the fourth camera remotely at the workspace.

19. A method for providing a video conference between a workspace and a remote participant at a monitor in a remote location, comprising the steps of:

displaying a presence view image of the remote participant on a first monitor in the workspace;

simultaneously displaying a shared space image showing a view in the remote location on a second monitor in the workspace, positioning a camera in the workspace focused on the second monitor; and transmitting the image of the second monitor to the remote location.

20. The method according to claim 19, further comprising the step of:

providing access from the workspace to a database contained in a memory.

21. The method according to claim 20, wherein the step of providing access includes the substep of selecting information from the database for display on the second monitor.

22. The method according to claim 21, wherein the step of providing access further includes the substep of modifying the information of the database in response to a pointing device.

23. The method according to claim 19, further comprising the steps of:

transmitting a presence view image of a participant in the workspace to the remote location;

transmitting the presence view image of the remote participant as provided by a camera to the first monitor; and transmitting the shared space image showing the view in the remote location to the second monitor.

24. The method according to claim 23, wherein the step of transmitting the presence view image of the remote participant includes the substeps of adjusting the position of the camera; and modifying the zoom of the camera.

25. The method according to claim 24, wherein the step of modifying the zoom of the camera includes changing the zoom of the camera remotely at the workspace.

* * * * *